United States Patent [19]

Geria et al.

[11] Patent Number: 4,511,554
[45] Date of Patent: Apr. 16, 1985

[54] NON-STAINING ANTIPERSPIRANT STICK COMPOSITION

[75] Inventors: Navin Geria, Warren; Chung T. Shin, Livingston, both of N.J.

[73] Assignee: Bristol-Myers Company, New York, N.Y.

[21] Appl. No.: 606,864

[22] Filed: May 4, 1984

Related U.S. Application Data

[63] Continuation of Ser. No. 387,390, Jun. 11, 1982, abandoned, which is a continuation-in-part of Ser. No. 155,688, Jun. 2, 1980, abandoned.

[51] Int. Cl.$^3$ .......................... A61K 7/32; A61K 7/34; A61K 7/36; A61K 7/38
[52] U.S. Cl. ........................................ 424/65; 424/66; 424/67; 424/68
[58] Field of Search ...................... 424/68, 66, 65, 67

[56] References Cited

U.S. PATENT DOCUMENTS

| | | | |
|---|---|---|---|
| 4,100,271 | 7/1978 | Krezanoski | 424/342 |
| 4,171,455 | 10/1979 | Tomita | 424/342 |
| 4,226,889 | 10/1980 | Yuhas | 424/59 |
| 4,268,498 | 5/1981 | Gedeon et al. | 424/59 |

*Primary Examiner*—Dale R. Ore
*Attorney, Agent, or Firm*—Gabriel P. Katona

[57] ABSTRACT

Essentially non-staining antiperspirant stick composition containing the combination polyoxyethylene(25) propylene glycol stearate and polyoxypropylene, polyoxyethylene ether of a long chain fatty alcohol; it may also contain a non-staining emollient system comprising a volatile silicone oil and/or dibutylphthalate.

8 Claims, No Drawings

NON-STAINING ANTIPERSPIRANT STICK COMPOSITION

RELATED CASES

This is a continuing application of application Ser. No. 387,390 filed June 11, 1982 which in turn is a continuation-in-part of application Ser. No. 155,688 filed June 2, 1980, both abandoned.

This invention relates to antiperspirant stick compositions. More particularly, it concerns compositions of this character which have low staining potential.

One of the problems associated with the use of antiperspirant stick compositions commonly found on the market is the staining problem. It is not uncommon for users of such stick products to find that after application and wear of these products their undergarments are stained with an oily stain. This is obviously an unsatisfactory state of affairs and reduces the consumer appeal for such products.

There are two aspects of the staining problems encountered with stick antiperspirant compositions. One is the ease with which the stain is removed from the clothes once it is formed. The second is the degree to which the formation of the stain can be avoided in the first instance. It has now been found that with respect to the first aspect of the problem that stains formed from antiperspirant stick compositions can be readily removed from clothes if there is incorporated in the stick composition a combination of polyoxyethylene(25)propylene glycol stearate and a polyoxypropylene, polyoxyethylene ether of a long chain fatty alcohol. As to the second aspect of the problem, it has been found that the staining potential in the first instance is reduced if the emollient system employed in the stick composition comprises dibutylphthalate or a volatile silicone oil, petroleum distillate, 2-ethylhexyl pelargonate, or a combination thereof.

It is accordingly an object of the present invention to provide an antiperspirant stick composition having a low potential for staining.

Other and more detailed objects of this invention will be apparent from the following description and claims.

Unless otherwise specified, the percentages given herein are in terms of percent by weight based on the total weight of the stick composition.

The polyoxyethylene(25)propylene glycol stearate employed in the present invention can be described by the formula:

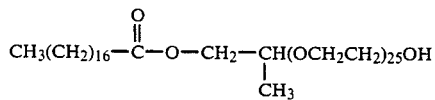

A commercially available product of this kind is marketed under the trade name G-2162 and is sold by ICI United States.

The quantity of polyoxyethylene(25)propylene glycol stearate that will be incorporated in the present compositions may vary somewhat. For the most part, this will comprise from about 1.0% to about 15.0% of the stick composition with the preferred range being from about 1.0% to about 5.0%.

The polyoxypropylene, polyoxyethylene ether of the long chain fatty alcohol that is employed for the present purposes can be described by the formula:

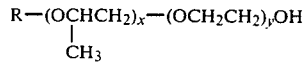

in which x and y are whole numbers. R is a long chain fatty alcohol moiety(e.g. cetyl, myristyl, stearyl). The value of x can range from 3 to 10 and the value of y can range from 2 to 50. The preferred range in the case of x it is 3 to 5 and for y it is 2 to 25. A material that is particularly suitable for the purposes of the present invention is a material of Formula II in which x has an average value of 5 and y has an average value of 20 and R is cetyl. A material of this type that is sold commercially is sold under the trade designation Procetyl AWS (Croda). Other commercially available materials which are suitable are Witconol APEM (PPG-3 Myreth-3), Witconol APES (PPG-9-Stearth-3), Standamul OXL (PPG-10-Cetearth-20), Procetyl AWS Modified (PPG-8-Ceteth-2).

This material also may be present in the instant composition over a range of amounts. Generally, it will comprise about 2.0% to about 40.0% of the stick with the preferred range being from about 5.0% to about 20.0%.

When ethoxylated emollient surfactants are used at or above 15% use level in the present antiperspirant stick products, the stick becomes soft and crumbles. However, we are able to incorporate up to 40% of the ethoxylated, propoxylated derivatives of fatty alcohol ethers and still retain hardness of the stick. This is unusual and unique contribution of these ingredients.

The stick compositions of the present invention may contain a non-polar emollient system which, when used together with polyoxyethylene(25)propylene glycol stearate and the polyoxypropylene, polyoxyethylene ether of a long chain fatty alcohol gives a low staining product. By way of example, mention may be made of fatty acid esters (isopropyl myristate, isopropyl palmitate), branched chain fatty acid esters (2-ethyl hexyl palmitate, 2-ethyl hexyl pelargonate), polyoxyalkylene glycol esters (polypropylene glycol 2000 monooleate), propylene glycol diesters of short chain fatty acids ($C_8$-$C_{10}$) (Neobee M-20), polyoxyethylene fatty acids, polyoxypropylene fatty ether (Procetyl), propoxylated lower alcohol ether (Fluid AP), higher fatty alcohols (oleyl, hexadecyl, lauryl, etc.), silicone oils (dimethyl polysiloxanes 10–1000 centistokes).

However, in a preferred form of this invention, it is useful to utilize a non-polar emollient system which is inherently non-staining. These include such materials as the volatile silicones (Cyclomethicone F-25 [SWS Co.], Cyclomethicone 7207 and 7158 [Union Carbide]); petroleum distillates (Shell Sol 71); dibutylphthalate and 2-ethylhexyl pelargonate or combinations thereof. The non-staining emollient system of choice is the combination of dibutylphthalate with a volatile silicone oil.

The quantity of non-polar emollient that may be contained in the present composition may vary somewhat. Usually, however, it will fall in the range of from about 30% to about 60%.

The quantity of dibutylphthalate that may be incorporated in the present sticks will vary depending upon whether it is the sole component of the emollient system or is used in conjunction with one or more other emollients. Generally, it will comprise between about 10.0% to about 45.0% of the stick, the preferred range being between about 25.0% to about 35.0%.

Typical of the volatile silicones that may be employed herein is a material that is generally referred to as Cyclomethicone. This is a cyclic dimethylpolysiloxane that conforms to the formula:

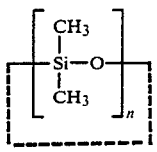

wherein n averages between 3 and 6.

As in the case with the other components of the present composition discussed above, the quantity of cyclomethicone contained in the sticks of this invention may also vary over a range. For the most part, this will fall between about 2.0% to about 10.0% of the stick. In the preferred forms of this invention, however, the cyclomethicone will comprise between about 5.0% and about 10.0% of the stick. A number of cyclomethicone products are available commercially. These include Volatile Silicone 7158 from Union Carbide and a host of others. (See for example CTFA Cosmetic Ingredient Dictionary, Second Edition, 1977, page 71 under the entry "Cyclomethicone").

As an optional feature, the compositions of this invention may also contain, as part of the emollient system, a water-soluble compound of the general formula:

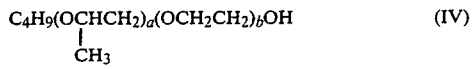

wherein a has an average value of from 2 to 33 and b has an average value of from 3 to 45. These compounds will be recognized as the UCONS of the HB series manufactured by Union Carbide. The preferred material is the compound of Formula IV in which a has an average value of 12 and b has the average value of 16 (CTFA nomenclature PPG-12-BUTETH-16). A material of this type is marketed commercially under the trade designation Ucon 50-HB-660.

It is also possible to employ the water-soluble UCONS of the 75H series. These are random copolymers prepared by the reaction of ethylene oxide and propylene oxide in various molar proportions. The number of moles of ethylene oxide employed vary in the range of from 17 to 125; whereas, the number of moles of propylene oxide vary from 4 to 50. Examples of these are PEG/PPG-17/6 Copolymer; PEG/PPG-18/4 Copolymer; PEG/PPG-23/50 Copolymer; PEG/PPG-35/9 Copolymer and PEG/PPG-125/30 Copolymer. The nomenclature used to identify these materials is in the CTFA Cosmetic Ingredient Dictionary, Second Edition. Similarly, other block copolymers known as Pluronics can also be used.

The quantity of "UCON" materials that may be employed herein will also vary somewhat. Usually, this will be in the range of from about 5.0% to about 50.0% of the stick with the preferred range being from about 30.0% to about 40.0%.

The principal active ingredient in the antiperspirant stick compositions of this invention is, of course, the powdered or solution form of antiperspirant material. This will ordinarily take the form of an astringent aluminum or zirconium compounds or complexes or mixtures thereof; that is, mixtures of aluminum compounds or mixtures of zirconium compounds or mixtures of aluminum compounds with zirconium compounds. Usually, the aluminum or zirconium compounds will take the form of astringent salts. Typical antiperspirant actives include impalpable aluminum chlorhydroxide and aluminum hydroxybromide, aluminum chloride as well as the aluminum/zirconium/glycine antiperspirant complexes disclosed in U.S. Pat. No. 3,792,068 issued Feb. 12, 1974 to Luedders et al.

The preferred aluminum compound for preparation of the Luedders et al complex is aluminum chlorhydroxide of the formula $Al_2(OH)_5Cl2H_2O$. The preferred zirconium compound for preparation of the Luedders et al complex is zirconyl hydroxychloride having the formula $ZrO(OH)Cl3H_2O$. The preferred amino acid for preparing the Luedders et al complex is glycine of the formula $CH_2(NH_2)COOH$. Salts of such amino acids can also be employed in such antiperspirant complexes.

Other suitable actives for use in the present invention comprise mixtures of aluminum chloride with other aluminum salts less acidic than aluminum chloride e.g. aluminum hydroxychloride (or aluminum chlorhydroxide). These are described in Canadian Pat. No. 958,338 issued Nov. 26, 1974.

The active antiperspirant material is generally present in the stick in powdered form suspended in the stick matrix. An antiperspirant active amount of this material will be employed. Ordinarily, this will constitute between about 10.0% and about 50.0% of the stick with the preferred range being between about 15.0% and 25.0%.

The backbone of the antiperspirant sticks of the present invention will generally comprise a low melting point waxy material that is a waxy material having a melting point of from about 100° F. to 150° F. Typical suitable low melting point waxes are fatty acids containing from about 8 to about 22 carbon atoms, fatty alcohols containing from about 8 to about 22 carbon atoms, silicone waxes and glycerol monostearate. Especially useful materials of this type are the $C_8$ to $C_{22}$ fatty acids and $C_8$ to $C_{22}$ fatty alcohols. By way of example, the following may be mentioned: cetyl alcohol, stearyl alcohol, myristyl alcohol, Lauryl alcohol and Behenyl alcohol. However, the preferred low melting point wax is stearyl alcohol.

The quantity of low melting point waxy material that may be contained in the present antiperspirant stick compositions may also vary somewhat. Ordinarily, this will comprise about 10.0% to about 35.0% by weight based on the total weight of the composition; the preferred range is from about 16% to 27% by weight.

The low melting point wax may be replaced in whole or in part by a high melting point wax. Suitable waxes are water-insoluble waxes having a melting point of from about 150° F. to about 215° F. Examples of suitable waxes are beeswax, spermaceti, carnauba, bayberry, candelilla, montan, ozokerite, ceresin, paraffin, castor wax, synthetic waxes such as Fischer-Tropsh waxes, and microcrystalline wax. The present compositions may contain from about 0.50% to about 10.0% of this wax. The preferred amount of high melting point wax is from about 2.0% to about 6.0%.

The antiperspirant stick compositions of this invention may also contain other ingredients commonly employed in other antiperspirant sticks or other forms of antiperspirant compositions. Thus, suspending agents, gelling agents, fillers, stabilizing agents, antioxidants, pigments, coloring agents, perfumes, preservatives, anti-bacterial agents, etc. may also constitute part of the present sticks.

The antiperspirant stick compositions of this invention may be made a variety of ways known to those skilled in the art. In one procedure, the emollient is first blended with the tinting agent, if any, e.g. titanium dioxide (Step 1). The antiperspirant, preferably in the form of a fine powder, is then mixed with the material made in Step 1 using light agitation and the temperature of this mixture is raised (Step 2). The waxy gelling agent, low melting point wax, surfactant and antioxidant are mixed together and heated to form a clear melt (Step 3). The contents of Step 2 and Step 3 are mixed together to form a homogeneous suspension which is used to fill the stick molds.

The following Examples are given to further illustrate the present invention. It is understood, however, that the invention is not limited thereto.

The following terms used in the specification and Examples have the meaning ascribed to them below:

PROCETYL AWS—Alkoxylated derivative of cetyl alcohol (PPG-5 Ceteth-20)

F-251 SILICONE—Volatile silicone consisting of mixture of low molecular weight cyclic dimethyl polysiloxanes Cyclomethicone F-251

FT-300 WAX—Paraffin Wax FT-300 (FT 300 Wax Dura)

G-2162—Polyoxyethylene(25)propylene glycol stearate

IONOL CP—Butylated hydroxytoluene

UCON 50-HB-660—PPG-12-Buteth-16 (Union Carbide)

FLUID AP—PPG-14-Butyl ether (Union Carbide)

DEP—Diethyl phthalate (DEP Union Camp)

SHELL SOL 71—Petroleum distillate (Shell Co.)

AZ 4—Al/Zr trichlorohydroxide

REZAL 410—Al/Zr trichlorohydrex-glycine

WITCO BASE—Glycol stearate

DRY FLO—Aluminum starch octenylsuccinate

MOD. AWS—PPG(8) Ceteth(2)

DBP—Dibutylphthalate

VOLATILE SILICONE—Cyclomethicone

The sticks were prepared using the general procedure described above.

EXAMPLE 1

| Formula FN 1534-16C | |
| --- | --- |
| | % W/W |
| Aluminum Chlorohydrate (UF) | 22.00 |
| Stearyl Alcohol | 27.00 |
| FT-300 Wax (Paraffin Wax) | 2.00 |
| G-2162 | 2.00 |
| Perfume 503248 | 1.00 |
| Ionol CP | 0.05 |
| Procetyl AWS | 20.00 |
| F-251 Silicone | 10.00 |
| Ucon 50-HB-660 | 15.95 |
| | 100.00 |

Product Stability: Stable at 110° F. for three weeks.

This composition was tested for staining potential using a standard staining study protocol developed in our laboratories. The results of this test are summarized in Table I below:

TABLE I

| Identification | T-shirts without sebum after 10 applications | T-shirts with sebum after 5 applications | Blue Cotton without sebum after 5 applications |
| --- | --- | --- | --- |
| Control (Water) | O.K. | Very slight | O.K. |
| Formula FN 1534-16C | O.K. | Very slight | O.K. Very slight stain |

TABLE II

| | % by Weight | | |
| --- | --- | --- | --- |
| Ingredient | Ex. 2 BL 1509-56 | Ex. 3 BL 1509-49 | Ex. 4 FN 1534-29 |
| Aluminum Chlorhydrate | 22.0 | 22.0 | 22.0 |
| Fluid AP | 5.0 | 5.0 | — |
| DEP | 23.70 | — | — |
| Procetyl AWS | 10.00 | 10.00 | 18.0 |
| Cyclomethicone F-251 | 7.00 | 7.00 | 7.0 |
| Shell Sol 71 | — | 21.70 | — |
| Stearyl alcohol | 27.00 | 29.00 | 25.0 |
| Ucon 50-HB-660 | — | — | 22.95 |
| FT 300 Wax | 2.00 | 2.00 | 2.00 |
| G-2162 | 2.00 | 2.00 | 2.00 |
| Ionol CP | 0.05 | 0.05 | 0.05 |
| Perfume | 1.00 | 1.00 | 1.00 |
| Titanium dioxide 328 | 0.25 | 0.25 | — |

Each of the above compositions were subjected to the fabric staining study described below.

Protocol

White cotton and cotton/polyester (65/35) fabrics representative of those used in wearing apparel are prepared. Woven fabrics are used. The specimens are cut to a size approximately 8 inches in the direction on the warp and 10 inches in the direction of the filling. Four sets of specimens are prepared, two for controls and two for treatment. One set of control specimens and one set of treatment specimens are pre-treated with artificial sebum. One set of control specimens and one set of treatment specimens are prepared as usual for International Fabric Institute (IFI) testing with no pre-treatment.

The pre-treated sets of fabric are treated by applying the artificial sebum to a 1 inch warp area in the center of the swatch and the full 10 inch filling area. Application is made by spraying the aerosol cans supplied for three seconds in a continuous movement three inches from the specimen. The initial burst from the aerosol can must be made in an area adjacent to the specimen to avoid lack of uniformity in the sebum coating. This initial burst is not timed; the three second interval commences as soon as the sebum spray beings to coat the specimen.

The two sets of treatment fabric are treated by applying the product to a 1 inch warp area in the center of the swatch and the full 10 inch filling area. For supplied products, 2 grams are used by pre-weighing the product and applying uniformly over the area. The fabric is hung on a line and allowed to dry at room temperature for a minimum of 16 hours or a maximum of 24 hours. The specimens are washed in a Kenmore home washer using the normal setting in warm water with a 4 pound load for cotton or cotton/polyester 65/35. AATCC detergent is added. Water is softened to zero hardness.

The samples are dried as usual for IFI testing, and then hand ironed using appropriate setting for the fabrics involved.

Fabrics are rated for staining by placing them over a black surface and comparing them to a set of Deering Milliken oil stains. These specimens are rated as 5 if no stain is present to a 1 if heavily stained. Quite often the stains will be yellow or there will be a residue other than the oil. This is noted.

The stain test is repeated four additional times for a total of five to determine if there is a buildup.

Performance Standards

There shall be no visible stains on white fabrics after laundering and treating five times:

| Code | 5 | No Stain |
|---|---|---|
| | 4 | Slight Stain |
| | 3 | Medium Stain |
| | 2 | Stain |
| | 1 | Heavy Stain |

The results of this test are summarized in Table III below:

TABLE III

| | Degree of Staining Following 5 Test Cycles | | | |
|---|---|---|---|---|
| | Without Sebum | | With Sebum | |
| Product | Cotton | Cotton/Polyester | Cotton | Cotton/Polyester |
| 2. BL 1509-56 | 5.0 | 5.0 | 5.0 | 5.0 |
| 3. BL 1509-49 | 5.0 | 5.0 | 5.0 | 5.0 |
| 4. FN 1534-29 | 4.8 | 5.0 | 5.0 | 5.0 |
| 5. Water | 5.0 | 5.0 | 5.0 | 5.0 |

It is clear from the above results that products 2, 3 and 4 in the Table were all free of any observed staining.

EXAMPLE 5

| FN 1534-16A | |
|---|---|
| | % W/W |
| Aluminum chlorohydrate | 22.00 |
| Stearyl alcohol | 27.00 |
| FT 300 Wax (Paraffin wax) | 2.00 |
| G-2162 (PEG-25 Propylene glycol stearate) | 2.00 |
| Perfume 503248 | 1.00 |
| Ionol CP | 0.05 |
| Procetyl AWS (Propoxy ethoxy cetyl alcohol) | 20.00 |
| Volatile Silicone F-251 | 10.00 |
| Ucon 50-HB-660 (Polyalkylene glycol) | 15.95 |
| | 100.00 |

EXAMPLE 6

| FN 1534-85 | |
|---|---|
| | % W/W |
| Dibutyl phthalate | 31.72 |
| Titanium dioxide | 0.23 |
| Volatile Silicone F-251 | 7.00 |
| Procetyl AWS | 10.00 |
| Perfume 503248 | 1.00 |

| FN 1534-85 -continued | |
|---|---|
| | % W/W |
| Aluminum chlorohydrate | 22.00 |
| Stearyl alcohol | 24.00 |
| FT 300 Wax | 2.00 |
| G-2162 | 2.00 |
| Ionol CP | 0.05 |
| | 100.00 |

EXAMPLE 7

| BL 1582-20A | |
|---|---|
| | % W/W |
| Stearyl alcohol | 27.00 |
| FT 300 Wax | 2.00 |
| G-2162 | 2.00 |
| Procetyl AWS | 10.00 |
| Ionol CP | 0.05 |
| 2-Ethyl hexyl pelargonate | 28.70 |
| Volatile Silicone F-251 | 7.00 |
| Titanium dioxide 328 | 0.25 |
| Aluminum chlorohydrate | 22.00 |
| Perfume 503248 | 1.00 |
| | 100.00 |

EXAMPLE 8

| FN 1624-89A | |
|---|---|
| | % W/W |
| Wikenol EO 346* | 18.75 |
| Aluminum zirconium trichlorohydrate (AZ-4 powder) | 10.00 |
| Stearyl alcohol | 20.00 |
| Volatile Silicone F-251 | 7.00 |
| Dibutyl phthalate (DBP) | 31.25 |
| FT 300 Wax | 2.00 |
| Perfume | 1.00 |
| G-2162 | 2.00 |
| Procetyl AWS | 10.00 |
| | 100.00 |

| | % |
|---|---|
| *$AlCl_3.6H_2O$ | 15.00 |
| $Mg(OH)_2$ | 3.75 |
| | 18.75 |

EXAMPLE 9

| FN 1624-90A | |
|---|---|
| | % W/W |
| Aluminum sesquichlorohydrate | 15.00 |
| Aluminum zirconium trichlorohydrate (AZ-4 powder) | 10.00 |
| Stearyl alcohol | 20.00 |
| Volatile Silicone F-251 | 7.00 |
| Dibutyl phthalate (DBP) | 33.00 |
| FT 300 Wax | 2.00 |
| G-2162 | 2.00 |
| Procetyl AWS | 10.00 |
| Perfume 503248 | 1.00 |
| | 100.00 |

EXAMPLE 10

BL 1685-37

| | % W/W |
|---|---|
| Dibutyl phthalate | 31.70 |
| Titanium dioxide | 0.25 |
| Volatile Silicone F-251 | 7.00 |
| Procetyl AWS (Modified) | 5.00 |
| Procetyl AWS | 10.00 |
| Perfume 503248 | 1.00 |
| Aluminum Zirconium trichlorohydrate | 22.00 |
| Stearyl alcohol | 19.00 |
| FT 300 Wax | 2.00 |
| G-2162 | 2.00 |
| Ionol CP | 0.05 |
| | 100.00 |

EXAMPLE 11

BA 1746-96

| | % W/W |
|---|---|
| Dibutyl phthalate | 31.70 |
| Titanium dioxide | 0.25 |
| Volatile Silicone F-251 | 7.00 |
| Procetyl AWS (Modified) | 5.00 |
| Procetyl AWS | 10.00 |
| Perfume 503248 | 1.00 |
| Aluminum Zirconium trichlorohydrate-glycine | 22.00 |
| Stearyl alcohol | 19.00 |
| FT 300 Wax | 2.00 |
| G-2162 | 2.00 |
| Ionol CP | 0.05 |
| | 100.00 |

The following Examples illustrate that the use of polyoxyethylene(25)propylene glycol stearate (i.e. G 2162) or an alkoxylated derivative of cetyl alcohol (e.g. PROCETYL AWS) alone as distinguished from a combination of the two in equivalent antiperspirant stick compositions show considerable differences in staining potential.

Two antiperspirant stick formulas containing PROCETYL AWS and a stain reducing component and identified as B.P. 1887-64 (P-1) and BL 1842-72A (P-2) were prepared. These had the following formulas:

| Ingredients | % by Wt. |
|---|---|
| B.P. 1887-64 (P-1) | |
| Montan OP Wax | 4 |
| Ozokerite Wax | 2 |
| DBP | 26 |
| PROCETYL AWS | 5 |
| Volatile Silicone | 8 |
| Dry Flo | 30.5 |
| Rezal 410 | 24 |
| BL 1842-72 (P-2) | |
| Stearyl Alcohol | 8 |
| Castor Wax | 6 |
| FT-300 Wax | 1 |
| Rezal 410 | 26 |
| DBP | 31 |
| PROCETYL AWS | 5 |
| Mod. AWS | 2.5 |
| Talc | 13 |

One antiperspirant stick formula containing G 2162 was prepared. This is identified as formula 1349 (G-1). This had the following formula:

| Ingredients | % by Wt. |
|---|---|
| 1349 (G-1) | |
| 2-Ethylhexyl palmitate | 45.72 |
| Titanium dioxide | 0.23 |
| Stearyl alcohol | 27.00 |
| Paraffin Wax FT-300 | 2.00 |
| PEG (25) Propylene Glycol Stearate (G 2162) | 2.00 |
| Butylated Hydroxytoluene | 0.05 |
| Aluminum Chlorohydrate Ultrafine Powder | 22.00 |
| Perfume 503248 | 1.00 |
| | 100.00 |

An antiperspirant stick composition representative of the present invention was also prepared containing both G 2162 and PROCETYL AWS. This was identified as Formula 1924 (P-G-1). This had the following formula:

| Ingredients | % by Wt. |
|---|---|
| Formula 1924 (P-G-1) | |
| AZ-4 | 22 |
| Stearyl alcohol | 10 |
| Witco base | 9 |
| FT-300 Wax | 2 |
| Dry Flo | 5 |
| G-2162 | 2 |
| PROCETYL AWS | 10 |
| Mod. AWS | 5 |
| DBP | 27 |
| Volatile silicone | 7 |

The protocol testing the staining potential for these products and the method of rating them is essentially the same as that described on pages 11 and 12 above. The results of these tests are summarized in the Table below:

TABLE II

| Product | Evaluation |
|---|---|
| BP 1887-64 (P-1) | Unacceptable high levels of stain on all fabrics tested |
| BP 1842-72A (P-2) | Unacceptable high levels of stain on all fabrics tested |
| 1349 (G-1) | Unacceptable levels of stain at all conditions |
| Formula 1924 (P-G-1) | Acceptable low levels of stain (less stain than commercial roll-on) |

Although the invention has been described with reference to specific forms thereof, it will be understood that many changes and modifications may be made without departing from the spirit of this invention.

What is claimed is:

1. An antiperspirant stick composition comprising a matrix and an antiperspirant quantity of active antiperspirant material distributed therein; said stick composition containing a mixture of polyoxyethylene(25)propylene glycol stearate of formula:

$$CH_3(CH_2)_{16}\overset{O}{\underset{\|}{C}}-O-CH_2-\underset{\underset{CH_3}{|}}{CH}(OCH_2CH_2)_{25}OH \qquad (I)$$

and a polyoxypropylene, polyoxyethylene ether of a long chain fatty alcohol of formula:

$$R-\underset{\underset{CH_3}{|}}{(OCHCH_2)_x}(OCH_2CH_2)_yOH \qquad (II)$$

wherein:
R is a long chain fatty alcohol moiety;
x has an average value of from 3 to 10; and
y has an average value of from 2 to 50
said mixture being present in sufficient quantity to reduce the staining potential of said composition; wherein said polyoxyethylene(25)propylene glycol stearate is present in the range of from about 1% to about 15% by weight and said polyoxypropylene, polyoxyethylene ether of said fatty alcohol is present in the range of from about 2% to about 40% by weight; said percentages being based on the total weight of the stick composition.

2. A composition according to claim 1 also comprising an emollient system containing an effective amount of an emollient selected from the group consisting of a volatile silicone oil, dibutylphthalate, petroleum distillate, 2-ethyl-hexyl pelargonate, and mixtures thereof.

3. A composition according to claim 2 in which said emollient system comprises from about 30% to about 60% by weight based on the total weight of the stick composition.

4. A composition according to claim 1 in which said polyoxyethylene(25)propylene glycol stearate is present in the range of from about 1% to about 5% by weight and said polyoxypropylene, polyoxyethylene ether of said fatty alcohol is present in the range of from about 5% to about 20% by weight; said percentages being based on the total weight of the stick composition.

5. A composition according to claim 1 in which said antiperspirant active material is present in the range of from about 10% to about 50% by weight based on the total weight of the composition.

6. A composition according to claim 5 in which said antiperspirant active material is present in the range of from about 15% to about 25% by weight based on the total weight of the composition.

7. A composition according to claim 1 in which said polyoxypropylene, polyoxyethylene ether of said long chain fatty alcohol is PPG-5 Ceteth-20.

8. An antiperspirant stick composition comprising a matrix and from about 15% to about 25% by weight of an active antiperspirant material distributed therein; said stick composition also containing from about 1% to about 5% by weight of polyoxyethylene(25)propylene glycol stearate of formula:

$$CH_3(CH_2)_{16}-\overset{O}{\underset{\|}{C}}-O-CH_2-\underset{\underset{CH_3}{|}}{CH}(OCH_2CH_2)_{25}OH \qquad (I)$$

from about 5% to about 20% by weight of PPG-5 Ceteth-20 and
from about 30% to about 60% by weight of an emollient system containing dibutylphthalate,
said combination of polyoxyethylene(25)propylene glycol stearate and said PPG-5 Ceteth-20 being present in sufficient quantity to significantly reduce the staining potential of said stick composition and said percentages being based on the total weight of said stick composition.

* * * * *